(12) United States Patent
Ahmad

(10) Patent No.: US 10,238,823 B2
(45) Date of Patent: Mar. 26, 2019

(54) GAS MIXING CONTROL APPARATUS AND METHOD

(75) Inventor: Samir Ahmad, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2314 days.

(21) Appl. No.: 13/257,652

(22) PCT Filed: Mar. 10, 2010

(86) PCT No.: PCT/IB2010/051044
§ 371 (c)(1),
(2), (4) Date: Sep. 20, 2011

(87) PCT Pub. No.: WO2010/109364
PCT Pub. Date: Sep. 30, 2010

(65) Prior Publication Data
US 2012/0006326 A1  Jan. 12, 2012

Related U.S. Application Data

(60) Provisional application No. 61/162,453, filed on Mar. 23, 2009.

(51) Int. Cl.
*A61M 16/00* (2006.01)
*A61M 16/10* (2006.01)
*A61M 16/12* (2006.01)

(52) U.S. Cl.
CPC ........ *A61M 16/024* (2017.08); *A61M 16/021* (2017.08); *A61M 16/022* (2017.08);
(Continued)

(58) Field of Classification Search
CPC .............. A61M 16/00; A61M 16/0003; A61M 16/0045; A61M 16/10; A61M 2016/102;
(Continued)

(56) References Cited

U.S. PATENT DOCUMENTS

2006/0201505 A1* 9/2006 Remmers et al. ....... 128/204.21
2007/0044799 A1* 3/2007 Hete et al. ............... 128/205.11
(Continued)

FOREIGN PATENT DOCUMENTS

JP  10-057492  3/1998
WO 2007008619 A2  1/2007
(Continued)

*Primary Examiner* — Colin W Stuart

(57) ABSTRACT

A ventilator includes first and second pathways, a conduit and a controller. The first pathway (120) is configured to supply a first gas and the second pathway (140) is configured to supply a second gas, where the second gas is mixed with the first gas to produce mixed gas having a predetermined percentage of the second gas. The conduit (166) is configured to provide the mixed gas from the first and second pathways to an access port during an inspiratory phase, and to provide discharged gas from the access port to the first pathway during an expiratory phase. The controller (180) is configured to delay supply of the second gas from the second pathway for a delay time in order to maintain the predetermined percentage of the second gas in the mixed gas provided to the access port during a subsequent inspiratory phase.

16 Claims, 3 Drawing Sheets

(52) U.S. Cl.
CPC ............ *A61M 16/10* (2013.01); *A61M 16/12* (2013.01); *A61M 16/0069* (2014.02); *A61M 16/107* (2014.02); *A61M 2016/0039* (2013.01); *A61M 2016/102* (2013.01); *A61M 2016/1025* (2013.01); *A61M 2202/0208* (2013.01)

(58) Field of Classification Search
CPC ........ A61M 2016/1025; A61M 16/021; A61M 16/022; A61M 16/024
USPC ............ 128/200.24, 203.12, 203.15, 203.25, 128/204.18, 204.21, 204.22, 205.11
See application file for complete search history.

(56) References Cited

U.S. PATENT DOCUMENTS

| | | | |
|---|---|---|---|
| 2007/0125374 A1* | 6/2007 | Smith et al. ............. | 128/203.12 |
| 2007/0163592 A1 | 7/2007 | Reinstadtler | |
| 2009/0167698 A1* | 7/2009 | Altas et al. .................. | 345/173 |

FOREIGN PATENT DOCUMENTS

| | | |
|---|---|---|
| WO | 2007033271 A1 | 3/2007 |
| WO | 2009003488 A2 | 1/2009 |

\* cited by examiner

GAS MIXING CONTROL APPARATUS AND METHOD

BACKGROUND AND SUMMARY

A ventilator delivers a flow of pressurized gas, such as air and/or a mixture of air and extra (supplemental) oxygen, to the airway of a patient in order to assist in or substitute for the patient's breathing. A ventilator operates cyclically, such that the gas is provided to the patient during an inspiratory phase (corresponding to inhalation) and received from the patient during a subsequent expiratory phase (corresponding to exhalation). In order to provide a mixture of air and extra oxygen, for example, the ventilator receives air through an air pathway and pure oxygen through a separate oxygen pathway, and thus controls respective levels of each gas to obtain the desired mixture, provided to the patient during the inspiratory phase.

Generally, the patient interacts with a ventilator through conduits or "limbs" which conduct gas flow. A single limb ventilator provides a single conduit for inspiratory and expiratory phases, meaning that the patient receives (pressurized) gas from the ventilator during inhalation and discharges gas to the ventilator during exhalation through the same conduit. Typically, the discharged gas is directed through the air pathway of the ventilator. When the inspiratory gas flow includes a mixture of air and oxygen, for example, the expiratory gas flow necessarily includes at least a portion of the extra oxygen, resulting in "oxygen contamination" in the air pathway. Therefore, during the subsequent cycle of the inspiratory gas flow, the gas from the air pathway includes a higher concentration of oxygen than pure air. When the gas from the air pathway is mixed with additional oxygen from the oxygen pathway, the mixed gas provided to the patient has a higher than desired concentration of oxygen.

In contrast, a double limb ventilator avoids oxygen contamination of the air pathway by providing separate conduits for inspiratory and expiratory gas flows. That is, the patient receives (pressurized) gas from the ventilator through a first limb during inhalation, and discharges gas to the ventilator (or outside the ventilator) through a separate second limb to during exhalation. However, the inclusion and maintenance of two separate conduits increases complexity and expense of the ventilator. For example, a valve must be included to direct the inspiratory and expiratory gas flows to the appropriate conduits for proper operation.

In one aspect of the invention, a ventilator includes first and second pathways, a conduit and a controller. The first pathway is configured to supply a first gas and the second pathway is configured to supply a second gas, where the second gas is mixed with the first gas to produce mixed gas having a predetermined percentage of the second gas. The conduit is configured to provide the mixed gas from the first and second pathways to an access port during an inspiratory phase, and to provide discharged gas from the access port to the first pathway during an expiratory phase. The controller is configured to delay supply of the second gas from the second pathway for a delay time in order to maintain the predetermined percentage of the second gas in the mixed gas provided to the access port during a subsequent inspiratory phase.

In another aspect of the invention, a ventilator includes air and oxygen pathways, a blower, a conduit and a controller. The air pathway is configured to supply air to a mixing node. The oxygen pathway is configured to supply oxygen to the mixing node, where the oxygen is mixed with air to obtain a mixed gas having a predetermined percentage of oxygen. The blower is configured to pressurize the mixed gas during an inspiratory phase. The conduit is configured to provide the pressurized mixed gas from the blower to an access port during the inspiratory phase, and to provide discharged gas from the access port to the air pathway during an expiratory phase. The controller is configured to delay supply of the oxygen gas from the oxygen pathway for a delay time in order to maintain the predetermined percentage of the oxygen in the mixed gas during a subsequent inspiratory phase.

In another aspect of the invention, a method is provided for controlling contents of a mixed gas provided to a patient by a single limb ventilator during an inspiratory phase, the mixed gas including a predetermined amount of extra oxygen mixed with air. The method includes measuring flow of a discharged gas through an air pathway during an expiratory phase, the discharged gas including at least a portion of the extra oxygen of the mixed gas; calculating a volume of the discharged gas based on the measured flow; determining a delay time based on the calculated volume; and stopping flow of oxygen from an oxygen pathway, separate from the air pathway, for the determined delay time in order to compensate for the portion of the extra oxygen in the discharged gas during a subsequent inspiratory phase.

DETAILED DESCRIPTION

In the following detailed description, for purposes of explanation and not limitation, example embodiments disclosing specific details are set forth in order to provide a thorough understanding of an embodiment according to the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known devices and methods may be omitted so as to not obscure the description of the example embodiments. Such methods and devices are clearly within the scope of the present teachings.

In the various embodiments, a single limb mechanical ventilator controls the amount of extra oxygen mixed with ambient air supplied to a patient. Following a cycle of inspiratory and expiratory phases of the ventilator, the amount of oxygen in a subsequent inspiratory phase is controlled by delaying oxygen flow for a predetermined period of time to compensate for excess oxygen in the air pathway (i.e., oxygen contamination) resulting from the expiratory phase of the previous cycle.

Figure 1:
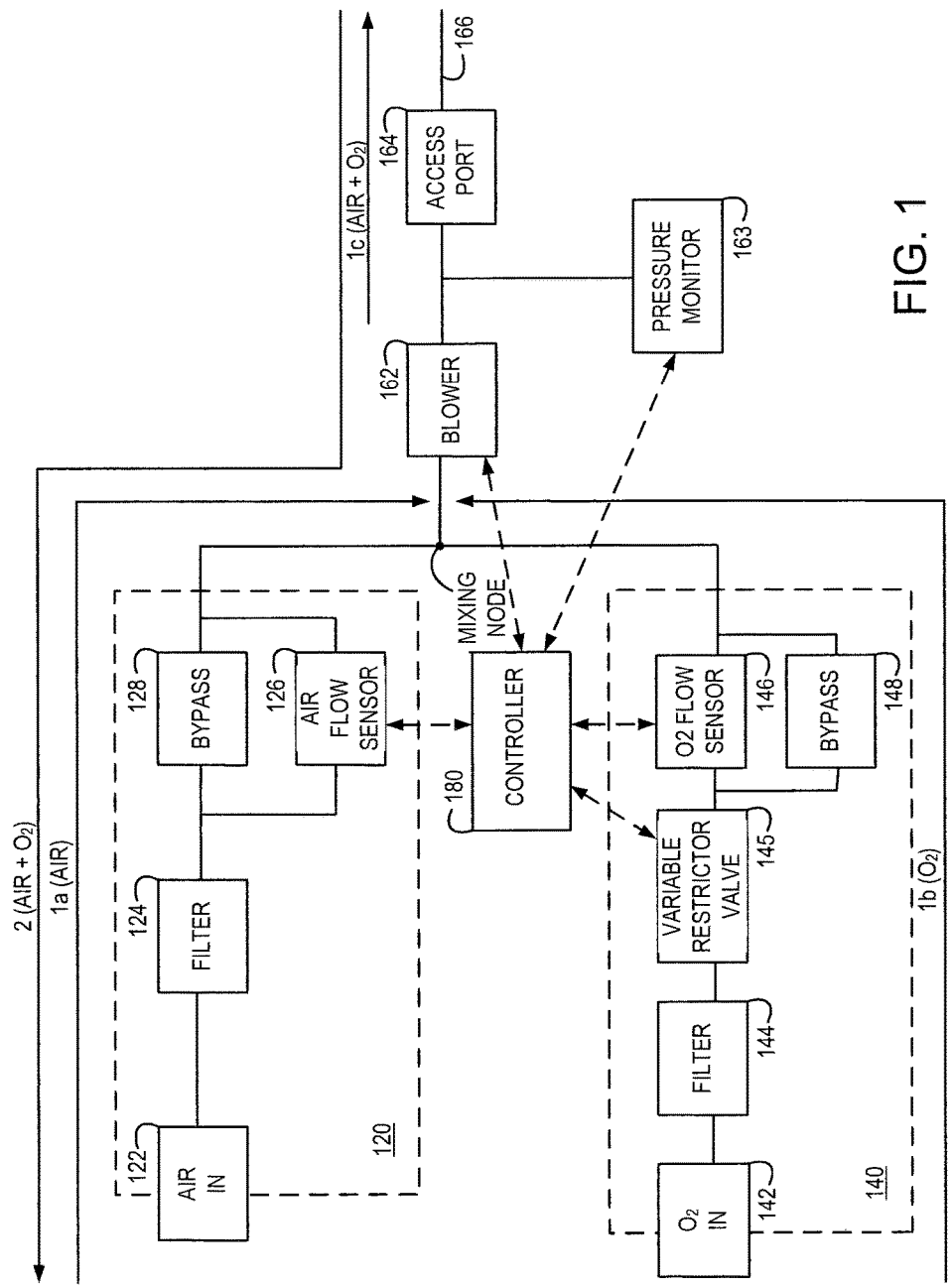
FIG. 1 is a functional block diagram of a single limb mechanical ventilator, according to a representative embodiment.

FIG. 1 is a functional block diagram of a single limb ventilator 100, according to a representative embodiment. For purposes of explanation, the gas mixing control process is directed to mixing air and oxygen in a ventilator system (e.g., as embodied by ventilator 100) for patient breathing assistance or substitution, although it is understood that the gas mixing control process may be directed to mixing other gases in ventilator or other systems without departing from the scope of the present teachings.

Referring to FIG. 1, the ventilator 100 includes air pathway 120 and oxygen pathway 140, which respectively supply ambient air and oxygen. The air and oxygen are mixed at mixing node 160 and provided to an input of blower 162. The amount of oxygen to be mixed with the air is determined based on the desired percentage or concentration of oxygen in the mixed gas, known as the fraction of oxygen in the inspired gas ($FiO_2$). The ventilator 100 enables the percentage of oxygen in the mixed gas to exceed 21 percent (up to 100 percent), depending on the $FiO_2$ set value. The percentage of oxygen in the mixed gas is controlled by adjusting the amount of oxygen supplied by the oxygen pathway 140, e.g., under control of controller 180, discussed below.

In the depicted embodiment, the air pathway 120 includes air inlet 122, air inlet filter 124, air flow sensor 126 and bypass element 128. During the inspiratory phase (indicated by arrows 1a, 1b and 1c of FIG. 1), the air inlet 122 draws in ambient air, which is filtered by the air inlet filter 124. The air is drawn into the air inlet 122 by operation of the blower 162, which creates a pressure differential during the inspiratory phase. In alternative embodiments, the air inlet 122 may include a pump or other means for independently drawing ambient air into the air pathway 120. A portion of the air is deflected to pass through the air flow sensor 126, which measures the flow rate of air passing through the air pathway 120. The remaining portion of the air passes through the bypass element 128. In the depicted embodiment, the air flow sensor 126 determines the flow rate of the deflected portion of air, which can then be extrapolated to determine the flow rate of the total amount of air in the air pathway 120, thus minimizing disruption of the air flow. Of course, other embodiments may incorporate any other types of air flow sensors without departing from the scope of the present teachings. The measured air flow may be provided by the air flow sensor 126 to the controller 180, which may determine the volume of air based on the measured air flow. Alternatively, the air flow sensor 126 may determine the volume of air.

The oxygen pathway 140 includes oxygen inlet 142, oxygen inlet filter 144, valve 145, oxygen flow sensor 146 and bypass element 148. The oxygen inlet 142 may be a high pressure oxygen inlet, for example, receiving pure oxygen from a pressurized oxygen tank, wall mounted oxygen system, or the like. The oxygen may be filtered by the oxygen inlet filter 144 during the inspiratory phase, although the oxygen inlet filter 144 may not be included in various embodiments. The valve 145 variably restricts the amount of oxygen allowed to pass through the oxygen pathway 140, e.g., under control of the controller 180. The valve 145 may be a proportional solenoid valve, for example. Variably restricting the flow of oxygen through the oxygen pathway 140 adjusts the amount of oxygen that will be mixed with the air from the air pathway 120 at the mixing node 160, thus determining the proportion of oxygen in the mixed gas (e.g., the ratio of air and extra oxygen).

After passing through the valve 145, a portion of the oxygen is deflected to pass through the oxygen flow sensor 146, which measures the flow rate and/or the volume of oxygen in the oxygen pathway 140. The remaining portion of the oxygen passes through the bypass element 148. As discussed above with respect to the air flow sensor 126, in the depicted embodiment, the oxygen flow sensor 146 determines the flow rate of the deflected portion of oxygen, which can then be extrapolated to determine the flow rate of the total amount of oxygen in the oxygen pathway 140, thus minimizing disruption of the oxygen flow. Of course, other embodiments may incorporate any other types of oxygen flow sensors without departing from the scope of the present teachings. The measured oxygen flow measured by the air flow sensor 146 may be provided to the controller 180.

The blower 162 receives the mixed gas from the mixing node 160 and outputs variably controlled pressurized mixed gas, which is supplied to access port 164, during the inspiratory phase. For example, the blower 162 may control the pressure within a range. The patient receives and inhales the mixed gas through a single conduit, including tubing circuit 166. The tubing circuit 166 includes a distal end attached to a breathing mask (not shown), or attached to an endotracheal tube or a tracheostomy tube (not shown) insertable into the patient's airway, for example. In various embodiments, flow of the mixed gas and/or blower speed may be controlled in addition to or instead of pressure.

The pressure is monitored by machine pressure sensor 163, which may provide the detected pressure to the controller 180 and/or the blower 162, so that adjustments may be made to the blower 162 to maintain the desired pressure. Likewise, to the extent the controller 180 or operator determines that a different pressure should be implemented, the controller 180 adjusts the blower 162, until the machine pressure sensor 163 indicates that the desired pressure has been obtained. In various embodiments, a pressure sensor may additionally or alternatively be located at the breathing mask or other patient connection.

During the expiratory phase (indicated by arrow 2 of FIG. 1), positive flow through the air pathway 120 and the oxygen pathway is discontinued, allowing the patient to exhale through the tubing circuit 166 and the access port 164. The exhaled or discharged gas passes through the blower 162 (which may pressurize the discharged gas at a discharged gas pressure), and through at least a portion of the air pathway 120. During the expiratory phase, some of the discharged gas may exit the ventilator 100, for example, through the air inlet 122 or other vent (not shown). However, all or a portion of the discharged gas will remain in the air pathway 120, e.g., when a subsequent inspiratory phase (indicated by arrows 1a, 1b and 1c of FIG. 1) begins. When that occurs, the discharged gas remaining in the air pathway 120 from the previous cycle includes a higher concentration of oxygen (e.g., from the previous inspiratory phase), resulting in "oxygen contamination." That is, when the discharged gas in the air pathway 120, which includes the higher concentration of oxygen, is mixed with the oxygen from the oxygen pathway 140 during the subsequent inspiratory phase at the mixing node 160, the resulting mixed gas provided to the patient will have a higher than desired oxygen content.

In order to offset the higher concentration of oxygen, the controller 180 causes the oxygen pathway 140 to delay for a period of time after the end of the expiratory phase before providing additional oxygen to the mixing node 160, e.g., pursuant to the subsequent inspiratory phase. This effectively washes out the additional oxygen that would otherwise be included in the mixed gas provided to the blower 162.

In an embodiment, the amount of extra oxygen in the discharged air may be estimated by measuring the reverse air flow through flow sensor 126 during the expiratory phase. The controller 180 receives the measured discharged gas flow, and calculates the volume of discharged gas present (e.g., temporarily stored) within the air pathway 120. The controller 180 may then compare the calculated volume of discharged gas to a predetermined threshold.

Whenever the calculated volume of discharged gas exceeds the threshold, the controller 180 reduces the oxygen flow from the oxygen pathway 140 by a predetermined volume (which may be the same as the threshold), for example, by delaying the flow of oxygen in the subsequent inspiratory phase, as discussed above, for a period of time required for the predetermined volume to pass. Whenever the calculated volume of discharged gas does not exceed the threshold, the controller 180 reduces the oxygen flow from the oxygen pathway 140 by an amount corresponding to the calculated volume. As an example, it may be assumed for purposes of explanation that the predetermined threshold is 200 ml. Thus, if the calculated volume of discharged gas is 500 ml, for example, the controller 180 may reduce the oxygen flow from the oxygen pathway 140 by 200 ml (e.g., by delaying output of oxygen from the oxygen pathway 140 for a period of time corresponding to the flow of 200 ml of oxygen). However, if the calculated volume of discharged gas is 100 ml, for example, the controller 180 may reduce the oxygen flow from the oxygen pathway 140 by 100 ml.

It is understood that the volume by which the oxygen flow is reduced and/or the time by which the oxygen flow is delayed may be determined by various means, without departing from the scope of the present teachings. For example, in an embodiment, the controller 180 may execute an algorithm relating the calculated volume of discharged gas to a specific amount of extra oxygen (e.g., on the assumption that oxygen content in the discharged gas is not diluted), and a corresponding volume reduction and/or time delay with respect to the oxygen flow in the subsequent inspiratory phase. In another embodiment, the air pathway 120 may include a sensor (not shown) configured to detect the actual percentage of oxygen in the discharged gas. The controller 180 may then use the detected percentage of oxygen to calculate a precise difference between the detected percentage and the desired percentage of oxygen, and base the corresponding volume reduction and/or time delay with respect to the oxygen flow in the subsequent inspiratory phase on the calculated difference.

As will be appreciated by those skilled in the art, one or more of the various "parts" shown in FIG. 1, particularly including the controller 180, may be physically implemented using a software-controlled microprocessor, hard-wired logic circuits, or a combination thereof. Also, while the parts are functionally segregated in FIG. 1 for explanation purposes, they may be combined variously in any physical implementation.

For example, the controller 180 may be implemented as a microprocessor configured to execute one or more software algorithms, including the gas mixing control process of the embodiments described herein, in conjunction with a memory (not shown), to provide the functionality of ventilator 100. That is, the controller 180 may include a non-volatile memory for storing executable software code that allows it to perform the various functions of ventilator 100 and the gas mixing control process, discussed herein.

Figure 2:
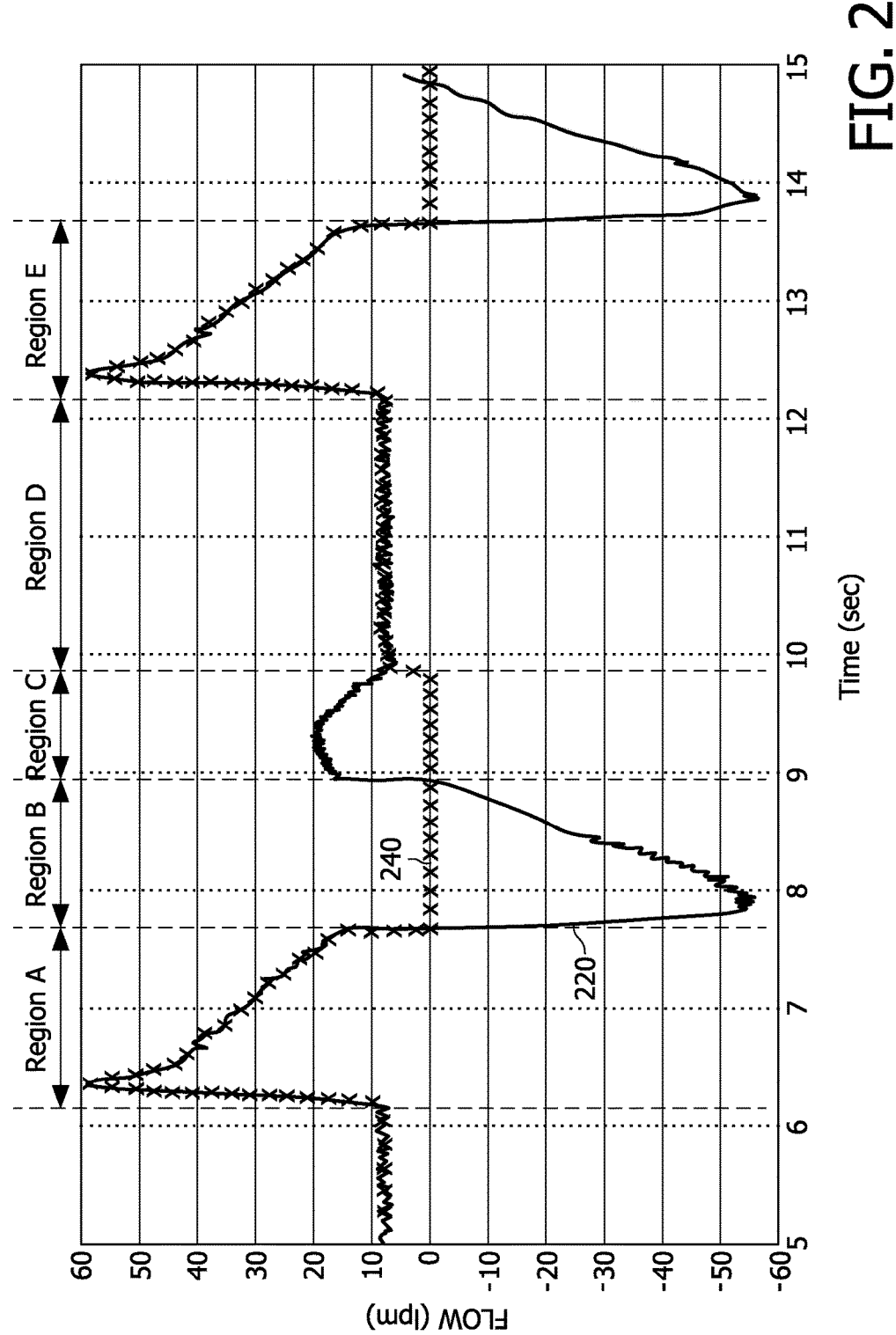
FIG. 2 is a chart showing air and oxygen flows, according to a representative embodiment.

FIG. 2 is a chart showing air and oxygen flow, according to a representative embodiment. The chart includes line 220 indicating air flow and line 240 (marked by x's) indicating oxygen flow through two consecutive inspiratory/expiratory gas flow cycles, e.g., as seen at respective flow sensors 126 and 146. The vertical axis indicates gas flow from −60 liters per minute (lpm) to +60 lpm in increments of 10 lpm, and the horizontal axis indicates time from 5 seconds to 15 seconds in increments of 1 second.

Referring to FIG. 2, region A depicts active inhalation in a first inspiratory phase, during which the patient inhales the mixed gas. Both air flow line 220 and oxygen flow line 240 indicate positive flow.

Region B depicts active exhalation in a first expiratory phase, during which the patient exhales the discharged gas (which is assumed to have about the same air and oxygen mixture as the inhaled mixed gas). Air flow line 220 indicates negative flow, since the discharged gas is directed through the air pathway 120 and thus only the flow sensor 126 detects the negative flow. Meanwhile, oxygen flow line 240 goes to zero, indicating that the supply of oxygen through the oxygen pathway 140 is shut down, e.g., via control of the valve 145, in region B.

Regions C and D depict positive flow, e.g., to compensate for leaks and to control to a set pressure. The patient has not yet begun physical inhalation of the subsequent inspiratory phase (i.e., indicated by region E). In region C, air flow line 220 indicates slightly positive flow, since the blower 162 operates to create the pressure differential after the negative air flow of the first expiratory phase ends. However, oxygen flow line 240 remains at zero, indicating that the supply of oxygen through the oxygen pathway 140 is still shut down. The time period covered by region C corresponds to the time by which the oxygen flow must be delayed in order for the oxygen contaminated air from the first expiratory phase (region B) to leave the air pathway 120. As discussed above, the length of the time period may determined by the controller 180 based on the volume of discharged gas sensed by the air flow sensor 126 during the first expiratory phase. In the depicted example, the air flow line 220 peaks slightly in region C to compensate for the lack of oxygen flow. In region D, the oxygen flow from the oxygen pathway 140 begins again for the upcoming inhalation, as indicated by the overlapping air flow line 220 and oxygen flow line 240. The depicted embodiment shows the time period during which oxygen flow is shut down (region C) as part of the expiratory phase, although it is understood that in other embodiments, the oxygen flow may be shut down during a portion of the subsequent inspiratory phase and/or between adjacent expiratory and inspiratory phases, without departing from the scope of the present teachings.

Region E depicts active inhalation in the second inspiratory phase, during which the patient again inhales the mixed gas, having the proper oxygen concentration. Both air flow line 220 and oxygen flow line 240 indicate positive flow. The cycle repeats with the patient's breathing process.

Figure 3:
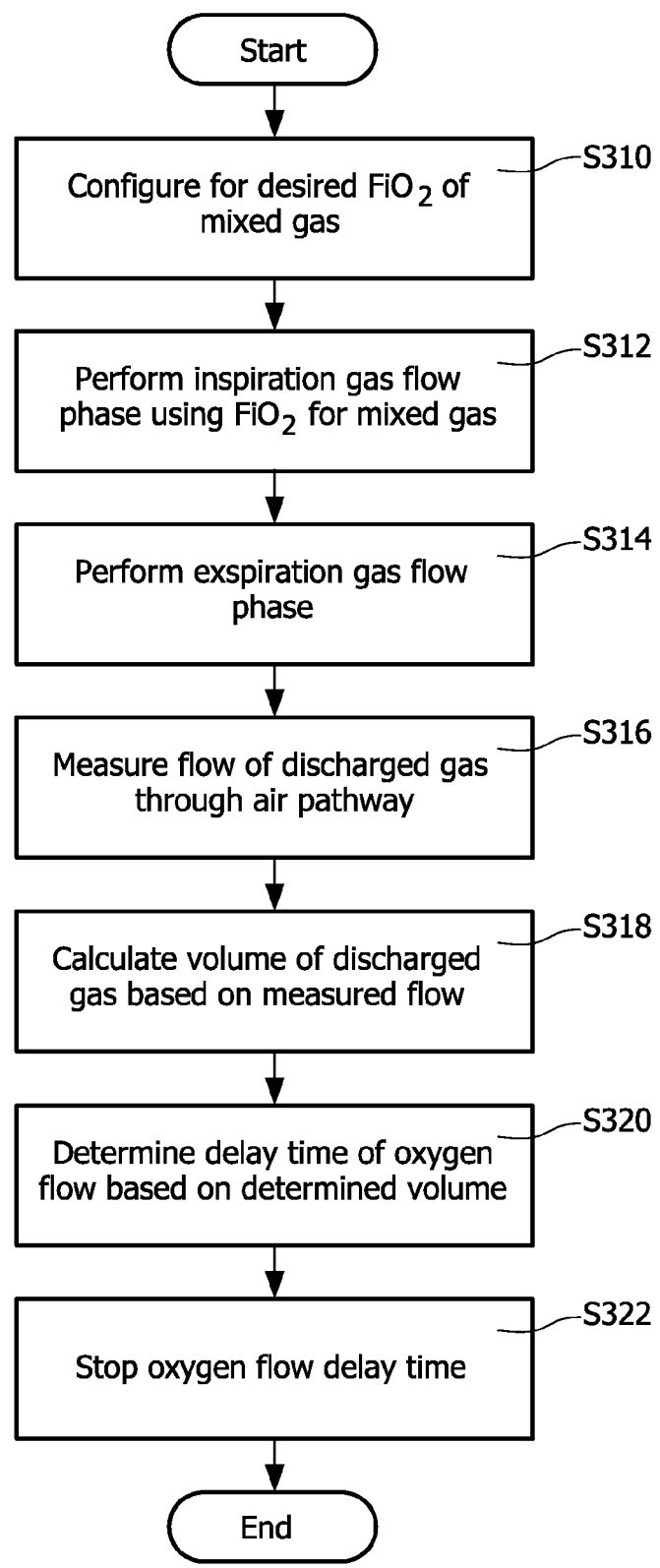
FIG. 3 is a flow chart of a gas mixing control process, according to a representative embodiment.

FIG. 3 is a flow chart of a gas mixing control process, according to a representative embodiment, which will discussed referencing FIGS. 1 and 2. All or a portion of the operations in FIG. 3 may be executed by or under control of the controller 180, for example.

In operation S310, the various elements of the ventilator 100 are configured based on the desired $FiO_2$ of the mixed gas to be supplied to the patient at the access point 164. For example, the valve 145 may be adjusted for the proper flow of oxygen through the oxygen pathway 140 that, when mixed with the air from the air pathway 120 at the mixing node 160, provides the desired proportion of oxygen in the mixed gas. Using the configuration of operation S310, an inspiratory phase is performed in operation S312 to provide the mixed gas (having the desired $FiO_2$) to the patient for inhalation via the access port 164.

In operation S314, an expiratory phase is performed. During the expiratory phase, the patient exhales discharged gas. The discharged gas flows into the air pathway 120, where the flow of the discharged gas is measured by the air flow sensor 126 and provided to the controller 180 in operation S316. The controller 180 calculates the volume of discharged gas based on the measured air flow in operation S318, for example.

In operation S320, the controller determines a delay time by which the oxygen flow from the oxygen pathway 140 is to be delayed during the next inspiratory phase. As discussed above, the delay time may be determined using any variety of techniques, including for example comparing the calculated volume to a threshold and delaying the oxygen flow by a predetermined time whenever the calculated volume exceeds the threshold. In operation S322, the oxygen flow is stopped for the delay time, for example, by temporarily shutting off oxygen flow through the valve 145, prior to inhalation by the patient during the next inspiratory phase. Due to the cyclical operation of the ventilator 100, operations S312 through S322 may then be repeated. Of course, any changes in the desired FiO$_2$ would require re-configuring the elements of the ventilator 100, as indicated in operation S310.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

What is claimed is:

1. A ventilator comprising:
    a first pathway configured to supply a first gas;
    a second pathway configured to supply a second gas, the second gas being mixed with the first gas to produce mixed gas comprising a predetermined percentage of the second gas;
    a conduit configured to provide the mixed gas from the first and second pathways to an access port during an inspiratory phase, and to provide discharged gas from the access port to the first pathway during an expiratory phase;
    a controller configured to delay supply of the second gas from the second pathway for a delay time in order to maintain the predetermined percentage of the second gas in the mixed gas provided to the access port during a subsequent inspiratory phase;
    wherein the first pathway comprises a first flow sensor, the first flow sensor being configured to determine a flow of the discharged gas received by the first pathway during the expiratory phase; and
    wherein the controller determines a volume of the discharged gas received by the first pathway during the expiratory phase based on the determined flow of the discharged gas.

2. The ventilator of claim 1, wherein the first gas comprises air and the second gas comprises oxygen.

3. The ventilator of claim 1, further comprising:
    a blower configured to pressurize the mixed gas during the inspiratory phase and to pressurize the discharged gas during the expiratory phase.

4. The ventilator of claim 1, wherein the controller determines the delay time based on the determined volume of the discharged gas.

5. The ventilator of claim 4, wherein the controller determines the delay time by comparing the determined volume of the discharged gas to a predetermined threshold.

6. The ventilator of claim 5, wherein the controller sets the delay time to equal a predetermined period of time by when the determined volume of the discharged gas exceeds the predetermined threshold.

7. The ventilator of claim 5, wherein the controller sets the delay time to equal a period of time corresponding to the determined volume of the discharged gas when the determined volume of the discharged gas does not exceed the predetermined threshold.

8. The ventilator of claim 4, wherein the second pathway comprises a valve configured to adjust the supply of the second gas under control of the controller.

9. The ventilator of claim 8, wherein the controller controls the valve to stop the supply of the second gas for the delay time.

10. The ventilator of claim 9, wherein the valve comprises a proportional solenoid valve.

11. A ventilator comprising:
    an air pathway configured to supply air to a mixing node;
    an oxygen pathway configured to supply oxygen to the mixing node, where the oxygen is mixed with air to obtain a mixed gas having a predetermined percentage of oxygen;
    a blower configured to pressurize the mixed gas during an inspiratory phase;
    a conduit configured to provide the pressurized mixed gas from the blower to an access port during the inspiratory phase, and to provide discharged gas from the access port to the air pathway during an expiratory phase; and
    a controller configured to delay supply of the oxygen gas from the oxygen pathway for a delay time in order to maintain the predetermined percentage of the oxygen in the mixed gas during a subsequent inspiratory phase.

12. The ventilator of claim 11, wherein the oxygen pathway comprises a valve, and wherein the controller controls the valve to stop the supply of the oxygen for the delay time.

13. The ventilator of claim 12 wherein the valve comprises a proportional solenoid valve.

14. A ventilator comprising:
    an air pathway configured to supply air to a mixing node;
    an oxygen pathway configured to supply oxygen to the mixing node, where the oxygen is mixed with air to obtain a mixed gas having a predetermined percentage of oxygen;
    a blower configured to pressurize the mixed gas during an inspiratory phase;
    a conduit configured to provide the pressurized mixed gas from the blower to an access port during the inspiratory phase, and to provide discharged gas from the access port to the air pathway during an expiratory phase; and
    a controller configured to delay supply of the oxygen gas from the oxygen pathway for a delay time in order to maintain the predetermined percentage of the oxygen in the mixed gas during a subsequent inspiratory phase, wherein the air pathway comprises an air flow sensor configured to determine a flow of the discharged gas received by the air pathway during the expiratory phase.

15. The ventilator of claim 14, wherein the controller determines a volume of the discharged gas received by the air pathway during the expiratory phase based on the determined flow of the discharged gas, and
    wherein the controller determines the delay time based on the determined volume of the discharged gas.

16. A method of controlling contents of a mixed gas provided to a patient by a single limb ventilator during an inspiratory phase, the mixed gas including a predetermined amount of extra oxygen mixed with air, the method comprising:

measuring flow of a discharged gas through an air pathway during an expiratory phase with an air flow sensor, the discharged gas including at least a portion of the extra oxygen of the mixed gas;

with a controller, calculating a volume of the discharged gas received by the air pathway during the expiratory phase based on the measured flow of discharged gas;

with the controller, determining a delay time based on the calculated volume; and with a valve, stopping flow of oxygen from an oxygen pathway, separate from the air pathway, for the determined delay time in order to compensate for the portion of the extra oxygen in the discharged gas during a subsequent inspiratory phase.

\* \* \* \* \*